United States Patent [19]

Smith

[11] 4,156,091
[45] May 22, 1979

[54] 11-DEOXY-11-HYDROXYMETHYL-6-HYDROXY-PGE₁ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 918,526

[22] Filed: Jun. 23, 1978

Related U.S. Application Data

[63] Continuation-in-part of Ser. No. 812,794, Jul. 5, 1977, Pat. No. 4,131,738.

[51] Int. Cl.² .......................................... C07C 177/00
[52] U.S. Cl. ................................... 560/121; 260/404; 260/408; 260/410; 260/410.5; 260/410.9 R; 260/413; 260/501.17; 562/503
[58] Field of Search ....................... 560/121; 562/503; 260/404, 408, 410, 410.5, 410.9 R, 413, 501.17

[56] References Cited

PUBLICATIONS

Johnson et al., Prostaglandins, 12, 915, (1976).

*Primary Examiner*—Robert Gerstl
*Attorney, Agent, or Firm*—Robert A. Armitage

[57] ABSTRACT

The present invention provides 11-deoxy-11-hydroxymethyl-6-hydroxy-PGE₁ compounds which are useful pharmacological agents. These analogs are useful as prostacyclin-like drugs.

37 Claims, No Drawings

11-DEOXY-11-HYDROXYMETHYL-6-HYDROXY-PGE₁ COMPOUNDS

CROSS REFERENCE TO RELATED APPLICATION

This application is a continuation-in-part of Ser. No. 812,794, July 5, 1977, now issued as U.S. Pat. No. 4,131,738.

The present invention relates to 11-deoxy-11-hydroxymethyl-6-hydroxy-PGE₁ compounds, the preparation and use of which are described in U.S. Ser. No. 812,794, filed July 5, 1977, now issued as U.S. Pat. No. 4,131,738 on Dec. 26, 1978.

The essential material constituting a disclosure of the instant invention is incorporated by reference here from U.S. Pat. No. 4,131,738.

I claim:

1. A prostacyclin analog of the formula

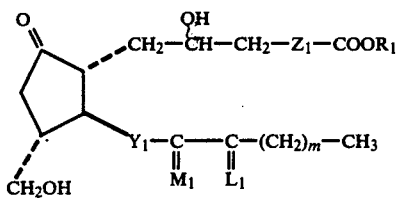

wherein $Z_1$ is
(1) $-(CH_2)_g-CH_2-CH_2-$,
(2) $-(CH_2)_g-CH_2-CF_2-$, or
(3) trans$-(CH_2)_g-CH=CH-$,
wherein g is the integer one, 2, or 3;
wherein $Y_1$ is
(1) trans$-CH=CH-$,
(2) cis$-CH=CH-$,
(3) $-CH_2CH_2-$,
(4) trans$-CH=C(Hal)-$, or
(5) $-C\equiv C-$,
wherein Hal is chloro or bromo;
wherein $M_1$ is

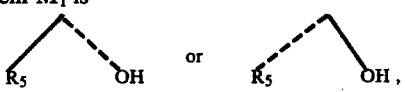

wherein $R_5$ is hydrogen or alkyl with one to 4 carbon atoms, inclusive;
wherein $L_1$ is

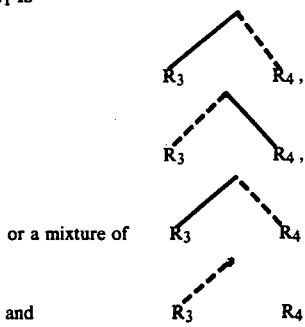

wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

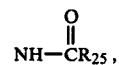   (a)

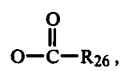   (b)

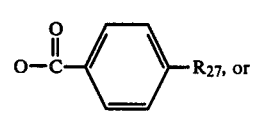   (c)

   (d)

wherein $R_{25}$ is methyl, phenyl, acetamidophenyl, benzamidophenyl, or $-NH_2$; $R_{26}$ is methyl, phenyl, $-NH_2$, or methoxy; and $R_{27}$ is hydrogen or acetamido, inclusive; or a pharmacologically acceptable cation;
wherein m is the integer one to 5, inclusive.

2. A prostacyclin analog according to claim 1, wherein $\sim$OH is beta.

3. 11-Deoxy-11-hydroxymethyl-6β-hydroxy-PGE₁, a prostacyclin analog according to claim 2.

4. A prostacyclin analog according to claim 1, wherein $\sim$OH is alpha.

5. 11-Deoxy-11-hydroxymethyl-6α-hydroxy-PGE₁, a prostacyclin analog according to claim 4.

6. 11-Deoxy-11-hydroxymethyl-6α-hydroxy-15-methyl-PGE₁, a prostacyclin analog according to claim 4.

7. 11-Deoxy-11-hydroxymethyl-6α-hydroxy-16,16-dimethyl-PGE₁, a prostacyclin analog according to claim 4.

8. 11-Deoxy-11-hydroxymethyl-6α-hydroxy-16,16-difluoro-PGE₁, a prostacyclin analog according to claim 4.

9. A prostacyclin analog according to claim 1, wherein $\sim$OH is a mixture of α-OH and β-OH.

10. A prostacyclin analog according to claim 9, wherein $Y_1$ is cis$-CH=CH-$.

11. 11-Deoxy-11-hydroxymethyl-6-hydroxy-cis-13-PGE₁, a prostacyclin analog according to claim 10.

12. A prostacyclin analog according to claim 9, wherein $Y_1$ is $-C\equiv C-$.

13. 11-Deoxy-11-hydroxymethyl-6-hydroxy-13,14-didehydro-PGE₁, a prostacyclin analog according to claim 12.

14. A prostacyclin analog according to claim 9, wherein $Y_1$ is trans$-CH=C(Hal)-$.

15. 11-Deoxy-11-hydroxymethyl-6-hydroxy-14-chloro-PGE₁, a prostacyclin analog according to claim 14.

16. A prostacyclin analog according to claim 9, wherein $Y_1$ is $-CH_2CH_2-$.

17. 11-Deoxy-11-hydroxymethyl-6-hydroxy-13,14-dihydro-PGE₁, a prostacyclin analog according to claim 16.

18. A prostacyclin analog according to claim 9, wherein $Y_1$ is trans-$CH=CH-$.

19. A prostacyclin analog according to claim 18, wherein $Z_1$ is $-(CH_2)_g-(CH_2-CF_2-$.

20. 11-Deoxy-11-hydroxymethyl-2,2-difluoro-6-hydroxy-15-methyl-PGE$_1$, a prostacyclin analog according to claim 19.

21. A prostacyclin analog according to claim 18, wherein Z$_1$ is trans—(CH$_2$)$_g$—CH=CH—.

22. 11-Deoxy-11-hydroxymethyl-trans-2,3-didehydro-6-hydroxy-PGE$_1$, a prostacyclin analog according to claim 21.

23. A prostacyclin analog according to claim 18, wherein Z$_1$ is —(CH$_2$)$_g$—CH$_2$—CH$_2$—.

24. A prostacyclin analog according to claim 23, wherein g is one.

25. A prostacyclin analog according to claim 24, wherein m is 3.

26. A prostacyclin analog according to claim 25, wherein R$_5$ is methyl.

27. 11-Deoxy-11-hydroxymethyl-6-hydroxy-15-methyl-PGE$_1$, a prostacyclin analog according to claim 26.

28. A prostacyclin analog according to claim 25, wherein R$_5$ is hydrogen.

29. A prostacyclin analog according to claim 28, wherein at least one of R$_3$ and R$_4$ is fluoro.

30. 11-Deoxy-11-hydroxymethyl-6-hydroxy-16,16-difluoro-PGE$_1$, a prostacyclin analog according to claim 29.

31. A prostacyclin analog according to claim 28, wherein at least one of R$_3$ and R$_4$ is methyl.

32. 11-Deoxy-11-hydroxymethyl-6-hydroxy-16,16-dimethyl-PGE$_1$, a prostacyclin analog according to claim 31.

33. A prostacyclin analog according to claim 28, wherein R$_3$ and R$_4$ are both hydrogen.

34. 11-Deoxy-11-hydroxymethyl-6-hydroxy-PGE$_1$, methyl ester, a prostacyclin analog according to claim 33.

35. 11-Deoxy-11-hydroxymethyl-6-hydroxy-PGE$_1$, tris(hydroxymethyl)aminomethane salt, a prostacyclin analog according to claim 33.

36. 11-Deoxy-11-hydroxymethyl-6-hydroxy-PGE$_1$, benzamidophenyl ester, a prostacyclin analog according to claim 33.

37. 11-Deoxy-11-hydroxymethyl-6-hydroxy-PGE$_1$, a prostacyclin analog according to claim 33.

* * * * *

UNITED STATES PATENT OFFICE
CERTIFICATE OF CORRECTION

Patent No. 4,156,091   Dated 22 May 1979

Inventor(s) Herman W. Smith

It is certified that error appears in the above-identified patent and that said Letters Patent are hereby corrected as shown below:

Column 1, lines 59-63, " $\underset{R_3 \quad R_4}{\diagup\diagup}$ " should read -- $\underset{R_3 \quad R_4}{\diagup\diagdown}$ --.

Column 2, line 69, "$-(CH_2)_g\!\!-\!\!(CH_2-CF_2-$" should read -- $-(CH_2)_g-CH_2-CF_2-$ --.

Signed and Sealed this

Twenty-seventh Day of November 1979

[SEAL]

Attest:

RUTH C. MASON
*Attesting Officer*

LUTRELLE F. PARKER
*Acting Commissioner of Patents and Trademarks*